United States Patent [19]

Sanderson et al.

[11] Patent Number: 5,146,030
[45] Date of Patent: Sep. 8, 1992

[54] PROCESS FOR OLIGOMERIZING OLEFINS USING HALOGEN-FREE TITANIUM SALTS OR HALOGEN-FREE ZIRCONIUM SALTS ON CLAYS

[75] Inventors: John R. Sanderson, Leander; John F. Knifton; Edward T. Marquis, both of Austin, all of Tex.

[73] Assignee: Texaco Chemical Company, White Plains, N.Y.

[21] Appl. No.: 733,794

[22] Filed: Jul. 22, 1991

[51] Int. Cl.$^5$ .............................. C07C 2/08; C07C 2/12
[52] U.S. Cl. .................................. 585/533; 585/520; 585/530; 502/84
[58] Field of Search ............... 585/533, 520, 530; 502/84

[56] References Cited

U.S. PATENT DOCUMENTS

| | | | |
|---|---|---|---|
| 4,048,109 | 9/1977 | Ryu | 502/181 |
| 4,108,920 | 8/1978 | Ryu | 585/530 |
| 4,110,410 | 8/1978 | Ryu | 585/510 |
| 4,831,202 | 5/1989 | Giusti | 585/533 |
| 4,948,768 | 8/1990 | Kukes | 502/63 |
| 4,962,262 | 10/1990 | Winter et al. | 585/512 |
| 5,003,125 | 3/1991 | Guisti | 585/530 |

FOREIGN PATENT DOCUMENTS 00176   1/1988  PCT Int'l Appl.
1489646 10/1977 United Kingdom.

Primary Examiner—Asok Pal
Assistant Examiner—P. Achutamurthy
Attorney, Agent, or Firm—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using cation-exchangeable layered clays that have been treated with a non-halogenated titanium salt or non-halogenated zirconium salt.

18 Claims, No Drawings

PROCESS FOR OLIGOMERIZING OLEFINS USING HALOGEN-FREE TITANIUM SALTS OR HALOGEN-FREE ZIRCONIUM SALTS ON CLAYS

BACKGROUND OF THE INVENTION

1. Field of the Invention

The invention relates to the preparation of synthetic lubricant base stocks, and more particularly to synthetic lubricant base stocks made by oligomerizing linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of a base stock is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a less hazardous catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants have discovered, surprisingly, that a high conversion of olefin to oligomer may be obtained by contacting the olefin with a catalyst prepared by treating a cation-exchangeable layered clay with a non-halogenated titanium salt or non-halogenated zirconium salt. Moreover, the process of the present invention results in a high percentage of trimer and higher oligomers, i.e., a low dimer to trimer ratio. A high proportion of trimer and higher oligomers is particularly desirable when preparing a synthetic lubricant base stock from decene. In the absence of the low dimer to trimer ratio obtained using the present invention, substantial decene dimer must be recycled and further oligomerized to prepare enough oligomers having sufficient molecular weight to obtain base stocks suitable for synthetic lubricants. In addition to being excellent catalysts, the treated clays of the present invention are less hazardous and more easily handled than $BF_3$. Further, the process of the present invention avoids processing problems attendant to using halogenated catalysts, which tend to form corrosive compounds in situ.

SUMMARY OF THE INVENTION

The invention relates to a process for the preparation of oligomers, comprising contacting at elevated temperature (1) a linear olefin containing from 10 to 24 carbon atoms with (2) a catalyst comprising a cation-exchangeable layered clay having been treated with a compound selected from the group consisting of non-halogenated titanium salts and non-halogenated zirconium salts. The invention further relates to a process for the preparation of oligomers, comprising contacting at elevated temperature (1) a linear olefin containing from 10 to 24 carbon atoms with (2) a catalyst comprising a smectite-type clay having been (a) acid-treated and (b) treated with a compound selected from the group consisting of non-halogenated titanium salts and non-halogenated zirconium salts. The invention also relates to a process for the preparation of oligomers, comprising contacting at elevated temperature (1) a linear olefin containing from 10 to 24 carbon atoms with (2) a catalyst comprising an acid-treated montmorillonite clay having been (a) treated with a compound selected from the group consisting of non-halogenated titanium salts and non-halogenated zirconium salts, and then (b) heat-treated at a temperature of about 100° C. or greater.

DESCRIPTION OF THE PREFERRED EMBODIMENTS

The olefin monomer feed stocks used in the present invention may be selected from compounds comprising (1) alphaolefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 14 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization reaction may be represented by the following general equation:

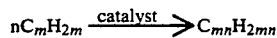

where n represents moles of monomer and m represents the number of carbon atoms in the monomer. Thus, the oligomerization of 1-decene may be represented as follows:

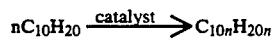

The reaction occurs sequentially. Initially, olefin monomer reacts with olefin monomer to form dimers. Some of the dimers that are formed then react with additional olefin monomer to form trimers, and so on. This results in an oligomer product distribution that varies with reaction time. As the reaction time increases, the olefin monomer conversion increases, and the selectivities for the heavier oligomers increase. An advantage of the present invention, particularly when using a preferred non-halogenated zirconium salt, is that a high percentage of trimer (relative to dimer) is observed. Generally, each resulting oligomer contains one double bond.

The oligomers may be prepared using cation-exchangeable layered clays that have been treated with non-halogenated titanium salts or non-halogenated zirconium salts. Silica-alumina clays, also called aluminosilicates, are useful cation-exchangeable layered clays. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties that afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

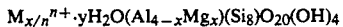

where M represents the interlamellar (balancing) cations, normally sodium or lithium; and x, y and n are integers. Engelhard Corporation's Grade F2C is an acceptable commercially available montmorillonite clay. Grade F2C has a moisture content at 220° F. of 16 wt. % and a pH of 7.5.

Optionally, cation-exchangeable layered clays, such as, for example, montmorillonite clays, may be acid-activated by such mineral acids as sulfuric acid, hydrochloric acid, and the like. Mineral acids activate montmorillonites by attacking and solubilizing structural cations in the octahedral layers. This opens up the clay structure and increases surface area. These acid-treated clays act as strong Bronsted acids. Suitable acid-treated clays include, for example, acidic calcium montmorillonite clays having a moisture content ranging up to about 20 wt. %, a residual acidity in the range of about 3 to about 30 mg KOH/g (when titrated to a phenolphthalein end point), and a surface area of about 300 m²/g or greater. Illustrative examples of commercially available acid-treated clays include Engelhard Corporation's Grade F24, having a moisture content of 12 wt. %, a residual acidity of 16 mg KOH/g, and a surface area of 350 m²/g; Grade F124, having a moisture content of 4 wt. %, a residual acidity of 14 mg KOH/g, a moisture content of 4 wt. %, a residual acidity of 14 mg KOH/g, and a surface area of 350 m²/g; Grade F13, having a moisture content of 12 wt. %, a residual acidity of 15 mg KOH/g, and a surface area of 300 m²/g; Grade F113, having a moisture content of 4 wt. %, a residual acidity of 15 mg KOH/g, and a surface area of 300 m²/g; and Grade F224, having virtually no moisture, and having a residual acidity of 5 mg KOH/g, and a surface area of 350 m²/g.

Thus, the clay component of the catalyst used in the present invention may comprise a neutral to basic clay (i.e. having a pH of about 7 or greater), or one that is acid-treated. It is preferred that the clay be acid-treated. If the clay component is to be acid-treated, acid treatment of the clay may be performed before treatment, during treatment, or after treatment with the non-halogenated titanium salt or non-halogenated zirconium salt.

Preferably, the clay is acid-treated before or during treatment with the non-halogenated titanium salt or non-halogenated zirconium salt. Thus, for example, a commercially pre-treated acid-activated clay, such as those Engelhard clays described above, may be further treated with a solution containing a non-halogenated titanium salt or non-halogenated zirconium salt. Alternatively, a neutral clay, such as Grade F2C, may be concurrently acid-treated and treated with the non-halogenated titanium salt or non-halogenated zirconium salt, in which case a quantity of titanium salt or zirconium salt is added with the clay to a dilute acid solution. The latter method is demonstrated in the examples that follow.

Where the clay has previously been acid-treated, it should be added to a solution of about 0.05 to about 25 wt. %, preferably from about 0.5 to about 10 wt. %, titanium salt or zirconium salt in water. The ratio of clay to titanium salt or zirconium salt solution should be sufficient to provide a catalyst having a quantity of titanium salt or zirconium salt deposited thereon ranging from about 0.05 to about 15 wt. %, preferably about 0.05 to about 5.0 wt. %. The clay should remain in the titanium salt or zirconium salt solution for a period of time and under 10 agitation to the extent necessary to meet these requirements, and then filtered and dried. Optionally, the filtered treated clay may be washed with distilled water before being dried, preferably under mild conditions.

If a titanium salt is chosen, it is preferred that it be selected from the group consisting of titanium sulfate, titanium citrate, titanium nitrate, and titanium phosphate. Of these titanium salts, titanium sulfate is preferred. Non-halogenated titanyl compounds also are acceptable titanium salts for purposes of this invention. If a zirconium salt is used to treat the clay, it is preferred that it be selected from the group consisting of zirconium sulfate, zirconium citrate, zirconium nitrate, and zirconium phosphate. Non-halogenated zirconyl compounds, such as zirconyl acetate, zirconyl carbonate, zirconyl sulfate, zirconyl nitrate, and the like, also are acceptable zirconium salts for purposes of this invention. Of the zirconium salts, zirconium sulfate is especially preferred. Zirconium salts are preferred over titanium salts where the lowest dimer to trimer ratio is desired. Other non-halogenated titanium and zirconium derivatives, such as titanium oxides and complexes and the like, and zirconium oxides and complexes and the like, also are useful for treating acid-treated cation-exchangeable layered clays.

Preferably, the catalyst is heat-treated before running the reaction. The catalyst may be heat-treated at temperatures in the range of about 50° to 400° C., with or without the use of a vacuum. A more preferred temperature range is 50° to 300° C. Heat-treatment at a temperature of about 100° to about 200° C. is especially preferred. Optionally, an inert gas may be used during heat-treatment as well. Preferably, the catalyst should be heat-treated under conditions and for a length of time which will reduce the water content of the catalyst to approximately 1 wt. % or less.

The oligomerization reaction may be carried out in either a stirred slurry reactor or in a fixed bed continuous flow reactor. The catalyst concentration should be sufficient to provide the desired catalytic effect. The temperatures at which the oligomerization may be performed are between about 50° and 300° C., with the preferred range being about 150° to 180° C., for optimum conversion. At temperatures of about 200° C. or greater, the amount of unsaturation remaining in the products of the oligomerization reaction may decrease, thus reducing the degree of hydrogenation necessary to remove unsaturation from the base stocks. However, at temperatures above 200° C., the olefin conversion may decrease and the dimer to trimer ratio to increase. Applicants have found that the addition of a hydrocarbon containing a tertiary hydrogen, such as methylcyclohexane, may further reduce the amount of unsaturation present in the base stocks. One skilled in the art may choose the reaction conditions most suited to the results desired for a particular application. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

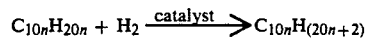

$$C_{10n}H_{20n} + H_2 \xrightarrow{\text{catalyst}} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the oligomers prior to hydrogenation and recycled to the catalyst bed for oligomerization. The removal or recycle of unreacted monomer or, if after hydrogenation, the removal of non-oligomerized alkane, should be conducted under mild conditions using vacuum distillation procedures known to those skilled in the art. Distillation at temperatures exceeding 250° C. may cause the oligomers to break down in some fashion and come off as volatiles. Preferably, therefore, the reboiler or pot temperature should be kept at or under about 225 ° C. when stripping out the monomer. Procedures known by those skilled in the art to be alternatives to vacuum distillation also may be employed to separate unreacted components from the oligomer.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention.

EXAMPLES

In the examples detailed below, the following procedures were used:

Preparation of Catalysts

Cat. #1: To 800 g of 10% sulfuric acid in a 2 liter beaker was added 180 g Engelhard's Grade F2C and 20 g titanium sulfate. The slurry was heated to 60°–80° C. and held at this temperature for 3.0 hours. The solid was allowed to settle and the acid poured off. A liter of demineralized water was added and the slurry stirred for 5.0 minutes. The solid was allowed to settle as before and the wash poured off. This procedure was repeated four more times and the solid collected with suction and washed with demineralized water until the wash was no longer acidic (by litmus paper.) The solid was then dried in an oven overnight at 100° C.

Cat. #2: Clay treated and dried as for Cat. #1 was further dried in an oven overnight at 200°–250° C.

Cat. #3: The procedure was identical to the procedure for Cat. #1, except that 20 g of zirconium sulfate was used instead of titanium sulfate.

Cat. #4: Clay treated and dried as for Cat. #3 was further dried in an oven overnight at 200°–250° C.

Cat. #5: To 800 g of 10% sulfuric acid in a 2 liter beaker was added 200 g Engelhard's Grade F2C. The slurry was heated to 60°–80° C. for 2.5 hours, and cooled to ambient temperature. The solid was allowed to settle and the acid poured off. A liter of demineralized water was added and the slurry stirred for 5.0 minutes. The solid was allowed to settle as before and the wash decanted. This procedure was repeated four more times and the solid collected with suction and washed with demineralized water until the wash was no longer acidic (by litmus paper.) The solid was then dried in an oven overnight at 200°–250° C.

Cat. #6: The procedure was identical to the procedure for Cat. #5, except that 180 g of Engelhard's Grade F2C was used, and 20 g of zirconium sulfate was added.

Oligomerization of Olefins

Olefin and catalyst were charged to a 250 ml three-necked flask equipped with an overhead stirrer, thermometer, heating mantle, and a water-cooled condenser ($N_2$ purge). The mixture was vigorously stirred and heated to the desired temperature for the desired time. The mixture was then cooled to ambient temperature and filtered with suction. The liquid was analyzed by liquid chromatography. The results obtained are detailed in Table I.

TABLE I

OLEFIN OLIGOMERIZATION WITH TREATED CLAYS

| Ex. No. | Olefin(s) (by carbon number) | (g) of Olefin | Catalyst | Amount of Catalyst (g) | Time/Temp. (Hr)/(°C.) | Olefin Con. (%) | M (%) | D (%) | T+ (%) | D/T+ Ratio |
|---|---|---|---|---|---|---|---|---|---|---|
| 1 | C-14 a | 100 | Grade F2C + Ti (cat. #1) | 10 | 5/160 | 68.5 | 31.5 | 50.9 | 15.9 | 3.20 |
| 2 | C-14 a | 100 | Grade F2C + Zr (Cat. #3) | 10 | 5/160 | 81.1 | 18.9 | 54.2 | 24.4 | 2.22 |
| 3 | C-14 a | 100 | Grade F2C + Ti (Cat. #2) | 10 | 5/160 | 61.6 | 38.4 | 41.0 | 19.6 | 2.09 |
| 4 | C-10 a | 100 | Grade F2C + Ti (Cat. #2) | 10 | 5/140 | 60.5 | 39.5 | 28.2 | 32.3 | 0.87 |
| 5 | C-10 a | 100 | Grade F2C + Zr (Cat. #4) | 10 | 5/140 | 71.0 | 29.0 | 28.7 | 42.3 | 0.68 |
| 6 | C-14 a | 100 | Grade F2C + Zr (Cat. #4) | 10 | 5/160 | 46.6 | 53.4 | 33.3 | 13.3 | 2.50 |
| 7 | C-14 a | 100 | Grade F2C + H (Cat. #5) | 10 | 5/160 | 72.0 | 28.0 | 42.5 | 27.7 | 1.53 |
| 8 | C-14 a | 100 | Grade F2C + Zr (Cat. #6) | 10 | 5/160 | 68.7 | 31.3 | 41.8 | 26.9 | 1.55 |
| 9 | C-10 a | 100 | Grade F2C + H (Cat. #5) | 10 | 5/140 | 70.4 | 29.6 | 36.1 | 34.3 | 1.05 |
| 10 | C-10 a | 100 | Grade F2C + Zr (Cat. #6) | 10 | 5/140 | 67.3 | 32.7 | 28.6 | 38.6 | 0.74 |

Con. = Conversion; M = Monomer; D = Dimer; and Trimer+ = Trimer + Tetramer + Pentamer, etc.

We claim:

1. A process for the preparation of oligomers, comprising contacting at elevated temperature (1) linear olefins containing from 10 to 24 carbon atoms with (2) a catalyst comprising a cation-exchangeable layered clay having deposited thereon a compound selected from the group consisting of titanium sulfate, titanium citrate, titanium nitrate, titanium phosphate, zirconium sulfate, zirconium citrate, zirconium nitrate, and zirconium phosphate.

2. The process of claim 1, wherein the cation-exchangeable layered clay is a smectite-type clay.

3. The process of claim 1, wherein the cation-exchangeable layered clay is a montmorillonite clay.

4. The process of claim 1, wherein the catalyst comprises a cation-exchangeable layered clay having deposited thereon a compound selected from the group consisting of titanium sulfate, titanium citrate, titanium nitrate, and titanium phosphate.

5. The process of claim 1, wherein the catalyst comprises a cation-exchangeable layered clay having deposited thereon a compound selected from the group consisting of zirconium sulfate, zirconium citrate, zirconium nitrate, and zirconium phosphate.

6. The process of claim 1, wherein the catalyst comprises a cation-exchangeable layered clay having deposited thereon titanium sulfate or zirconium sulfate.

7. The process of claim 1, wherein the catalyst is heat-treated at a temperature of about 100° to about 200° C. prior to being contacted with the olefins.

8. A process for the preparation of oligomers, comprising contacting at elevated temperature (1) linear olefins containing from 10 to 24 carbon atoms with (2) a catalyst comprising a smectite-type clay having been (a) acid-treated and (b) treated with a compound selected from the group consisting of titanium sulfate, titanium citrate, titanium nitrate, titanium phosphate, zirconium sulfate, zirconium citrate, zirconium nitrate, and zirconium phosphate so as to deposit the compound on said clay.

9. The process of claim 8, wherein the catalyst comprises a smectite-type clay having been (a) acid-treated and (b) treated with a compound selected from the group consisting of titanium sulfate, titanium citrate, titanium nitrate, and titanium phosphate so as to deposit the compound on said clay.

10. The process of claim 8, wherein the catalyst comprises a smectite-type clay having been (a) acid-treated and (b) treated with a compound selected from the group consisting of zirconium sulfate, zirconium citrate, zirconium nitrate and zirconium phosphate so as to deposit the compound on said clay.

11. The process of claim 8, wherein the catalyst comprises a smectite-type clay having been (a) acid-treated and (b) treated with a compound selected from the group consisting of titanium sulfate and zirconium sulfate so as to deposit the compound on said clay.

12. The process of claim 8, wherein the smectite-type clay is a montmorillonite clay.

13. The process of claim 8, wherein the olefins are contacted with the catalyst at a temperature of from about 150° C. to about 180° C.

14. The process of claim 8, wherein the catalyst is a montmorillonite clay having been (a) treated with an acid selected from the group consisting of sulfuric acid and hydrochloric acid, and l(b) treated with a compound selected from the group consisting of titanium sulfate, titanium citrate, titanium nitrate, titanium phosphate, zirconium sulfate, zirconium citrate, zirconium nitrate, and zirconium phosphate so as to deposit the compound on said clay.

15. The process of claim 8, wherein the catalyst is a montmorillonite clay having been treated with sulfuric acid and (b) treated with a compound selected from the group consisting of titanium sulfate and zirconium sulfate so as to deposit the compound on said clay.

16. A process for the preparation of oligomers, comprising contacting at elevated temperature (1) linear olefins containing from 10 to 24 carbon atoms with (2) a catalyst comprising an acid-treated montmorillonite clay having been (a) treated with a compound selected from the group consisting of titanium sulfate, titanium citrate, titanium nitrate, titanium phosphate, zirconium sulfate, zirconium citrate, zirconium nitrate, and zirconium phosphate so as to deposit the compound on said clay, and then (b) heat-treated at a temperature of about 100° to about 200° C.

17. The process of claim 16, wherein the catalyst comprises an acid-treated montmorillonite clay having been (a) treated with a compound selected from the group consisting of titanium sulfate and zirconium sulfate so as to deposit the compound on said clay, and then (b) heat-treated at a temperature of about 100° to about 200° C.

18. The process of claim 16, wherein the catalyst comprises an acid-treated montmorillonite clay having been (a) treated with a compound selected from the group consisting of zirconium sulfate, zirconium citrate, zirconium nitrate, and zirconium phosphate so as to deposit said compound on said clay, and then (b) heat-treated at a temperature of about 100° to about 200° C.

* * * * *